United States Patent [19]
Wei et al.

[11] Patent Number: 5,653,246
[45] Date of Patent: *Aug. 5, 1997

[54] DENTAL FLOSS HOLDER

[76] Inventors: Kuang-Hsing Wei; Kuang-Hung Wei, both of 18500 Bay Leaf Way, Germantown, Md. 20874

[*] Notice: The term of this patent shall not extend beyond the expiration date of Pat. No. 5,570,710.

[21] Appl. No.: 581,372

[22] Filed: Dec. 29, 1995

Related U.S. Application Data

[63] Continuation-in-part of Ser. No. 528,889, Sep. 15, 1995, Pat. No. 5,570,710, and Ser. No. 552,695, Nov. 3, 1995, abandoned.

[51] Int. Cl.[6] .................................................. A61C 15/00
[52] U.S. Cl. .......................... 132/323; 132/326; 132/327; 132/328
[58] Field of Search .................................. 132/321, 323, 132/324, 326, 327, 328, 329

[56] References Cited

U.S. PATENT DOCUMENTS

| | | | |
|---|---|---|---|
| 4,050,470 | 9/1977 | Miller | 132/323 |
| 4,403,625 | 9/1983 | Sanders et al. | 132/323 |
| 4,638,824 | 1/1987 | De La Hoz | 132/323 |
| 5,435,330 | 7/1995 | Dix | 132/323 |
| 5,503,168 | 4/1996 | Wang | 132/323 |

*Primary Examiner*—Gene Mancene
*Assistant Examiner*—Pedro Philogene

[57] ABSTRACT

A dental floss holder for securely fastening one end of a dental floss instead of winding it around a finger includes a first member, two mating surfaces, and a connector member. The dental floss is retained on the first member. One of the mating surfaces is formed on the first member and the other mating surface on the connector member. The connector member connects with first member so as to abut the mating surfaces closely against each other to fasten the dental floss. A slot and a notch are also provided to facilitate the retaining of the dental floss on the first member.

26 Claims, 3 Drawing Sheets

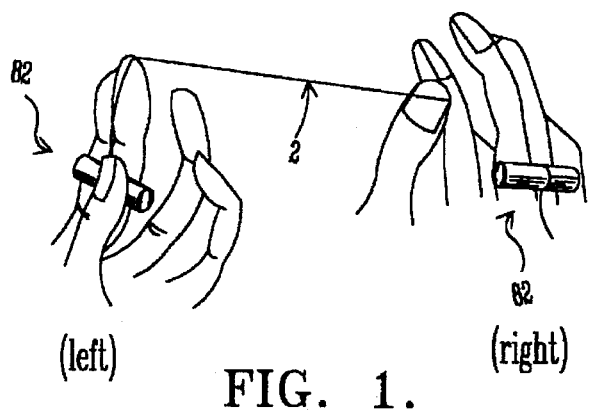
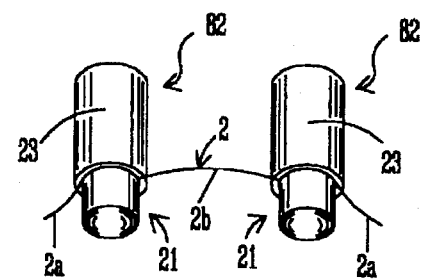
FIG. 1.     FIG. 2.
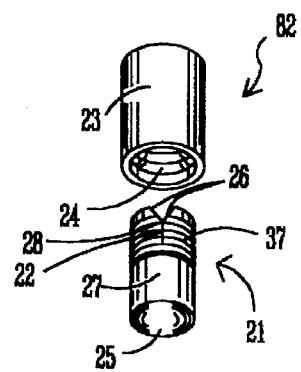
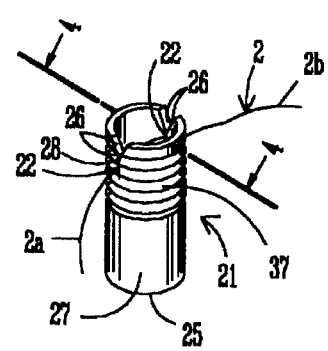
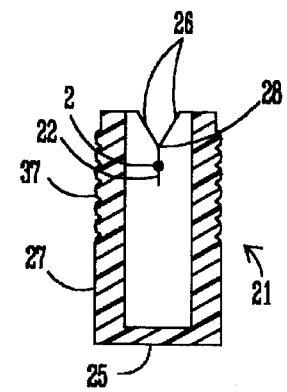
FIG. 3.     FIG. 4.     FIG. 5.
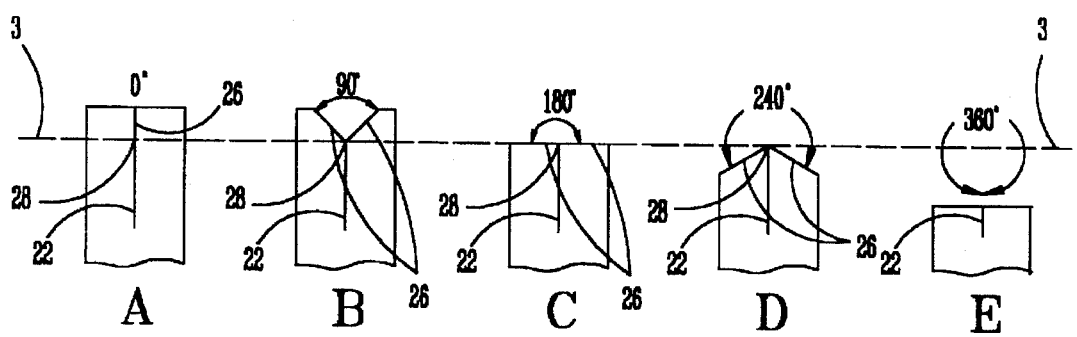
FIG. 6.

ns. 5,653,246

DENTAL FLOSS HOLDER

CROSS REFERENCE TO RELATED APPLICATIONS

This application is a continuation-in-part of U.S. application Ser. No. 08/528,889 filed Sep. 15, 1995, U.S. Pat. No. 5,570,710 and Ser. No. 08/552,695 filed Nov. 3, 1995 now abandoned.

BACKGROUND OF THE INVENTION

1. The Field of the Invention

This invention relates to the teeth cleaning with a length of dental floss and provides as its general object an improved device which is used to securely fasten dental floss and to render teeth-cleaning more effectively.

2. Description of the Prior Art

There are many devices attempting to render flossing less tedious and make it more effective and convenient. Moreover, a growing number of dentists and orthodontists recommend highly for cleaning teeth daily by using dental floss to remove food particles between teeth. However, most people still don't floss daily, even those who take teeth-cleaning and dental care seriously. The inconvenience and discomfort for maneuvering the dental floss by winding ends of a length of dental floss around two fingers is the main reason. The winding ends of a length of dental floss around two fingers will not only cause discomfort on fingers but also render difficulties in manipulating in mouth. Although there are numerous devices with a predetermined length of floss fixed in two-pronged dental devices, maneuvering with two fingers winding a length of dental floss is still the most effective way of daily dental floss cleaning, especially for reaching and positioning between the rear most teeth, and is highly recommended by the dental profession. U.S. Pat. No. 4,950,470 to Miller (1977) provides a dental floss holder with an inwardly tapered slot extending along one elongate edge which does not fasten the dental floss securely in place to facilitate the manipulating of the floss in mouth. U.S. Pat. No. 4,638,824 to De La Hoz (1987) provides a pair of dental floss finger rings having three cut out prongs for retaining a length of dental floss. The retaining prongs are prone to cut the floss at the retaining point as a result of strong force applied during flossing. Also, the floss tends to be pull out of the prongs during flossing operation which requires different angles for inserting floss in between teeth at different positions.

SUMMARY OF THE INVENTION

It is a general object of the invention to provide a dental floss holder and a method for fastening one end of a dental floss. A dental floss holder for securely fastening one end of a dental floss instead of winding it around a finger includes a first member, two mating or corresponding surfaces, and a connector member. In the present invention, the dental floss is retained on the first member. One of the mating surfaces is formed on the first member and the other mating surface on the connector member. The connector member connects with the first member such that there is substantially no gap or space between the mating surfaces so that the mating surfaces abut against each other closely to fasten the dental floss. A slot and a notch are also provided to facilitate the retention of the dental floss on the first member.

The method of the invention includes first retaining the dental floss onto the first member. It then follows by connecting the connector member with the first member so as to fasten the two mating surfaces together to securely, tightly fasten the dental floss between the two mating surfaces. The method also includes the steps of receiving the dental floss into the notch and the slot.

Accordingly, several objects and advantages of the present invention are:

(a) to provide an improved dental floss holder which is used to eliminate the discomfort caused by winding a length of dental floss around fingers;

(b) to provide an improved dental floss holder which is designed to save the wasteful of floss for winding an extra length of dental floss around fingers;

(c) to provide an improved dental floss holder to securely fasten dental floss ends than wind around fingers which is needed to be rewound several times during the course of teeth-cleaning; and (d) to provide an improved dental floss holder to better control of a strained floss and perform a more effective teeth-cleaning.

Further objects and advantages of the invention will become apparent from the appended drawings and the ensuing specifications.

DRAWING FIGURES

FIG. 1 is a perspective view showing the use of the dental floss holders with a dental floss fastened on each holder;

FIG. 2 is a perspective view of the dental floss holders, shown in FIG. 1, connecting in pairs with a dental floss;

FIG. 3 is a perspective view of the new dental floss holder;

FIG. 4 is a perspective view of the first member in FIG. 3 with a dental floss;

FIG. 5 is a sectional elevation of the first member in position taken on the line 4—4 of FIG. 4;

FIGS. 6A–6E is an illustration of a notch at different angles with a slot in FIG. 5;

DETAILED DESCRIPTION OF THE PREFERRED EMBODIMENT

Figure 7:
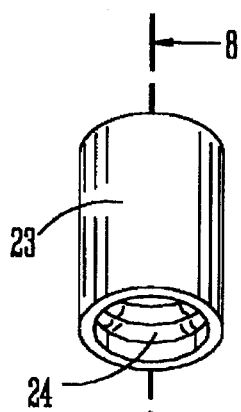
FIG. 7 is a perspective view of the connector member in FIG. 3.

Referring to FIGS. 1 and 2, it illustrates that a length of conventional dental floss 2 connects two identical dental floss holders 82. Dental floss 2 includes a section 2b and two sections 2a. Each section 2a defines each end of dental floss 2. Section 2b defines the portion of dental floss 2 between dental floss holders 82 and connects both holders 82. Each dental floss holder 82 is easily manipulated by each hand so that dental floss 2 is ready to be used inside mouth to clean teeth (not shown) as one usually does with both ends of a dental floss winding around fingers. One of dental floss holders 82 may be held by one hand, as shown in left of FIG. 1, and the other holder may be supported by the back of the other hand, as shown in right of FIG. 1, to clean teeth. Dental floss holders 82 provide much better control of dental floss 2 and eliminate the discomfort by winding ends of a dental floss around fingers. A single holder may be used on one hand with the opposite end of the dental floss fastened by some other means or by fingers; however, it is expected that two holders will be used. Dental floss holder 82 is suitable for use with the conventional thread or cord type of dental floss or with ribbon or band type of floss. It should be understood that the term "dental floss" is used generically to indicate any type of floss.

Referring now to FIGS. 3, 4, and 5, each dental floss holder 82 comprises retaining means for retaining each end of dental floss 2. In the preferred form of the present invention the retaining means comprises a first member 21 which preferably comprises a generally elongated cylindrical piece of material dimensioned to be easily handled by fingers for retaining dental floss 2 onto first member 21. First member 21 has a bottom 25 defining the bottom of first member 21.

Referring again to FIGS. 3, 4, and 5, each dental floss holder 82 also comprises first receiving means for receiving each end of dental floss 2 to facilitate the retention of dental floss 2. In the preferred form of the invention the first receiving means comprises a notch 26 defining an angular cut opening through substantially the opposite end of bottom 25. Each dental floss holder 82 further comprises second receiving means for further receiving each end of dental floss 2 after dental floss 2 is received by the first receiving means to further facilitate the retention of dental floss 2. In the illustrated form of the invention the second receiving means comprises a slot 22 for further receiving dental floss 2. Slot 22 connects with notch 26 preferably at a connection line 28 defining a line where the angular cut of notch 26 converges or meets together so that the only action required to insert dental floss 2 from notch 26 into slot 22 is a downward force to pull dental floss 2 into slot 22.

Referring particularly to FIGS. 3, 5, 8, 9, and 10, each dental floss holder 82 further comprises fastening means for fastening each end of dental floss 2. The fastening means comprises two mating or corresponding surfaces to be able to abut against each other closely, tightly together without substantially any gap or space therebetween to securely fasten each end of dental floss 2. In this form of the invention the fastening means comprises an inner surface 24 and an outer surface 27. Inner surface 24 and outer surface 27 are configured to have mating or corresponding dimensions so that when both surfaces are matingly joined, inner surface 24 and outer surface 27 abut against each other closely, tightly together without substantially any gap or space therebetween. Consequently, the cross-sectional dimension of dental floss 2 is then compressed or flattened between inner surface 24 and outer surface 27. Therefore, the closely abutted inner surface 24 and outer surface 27 are to effectively clamp the compressed dental floss 2 and to securely fasten dental floss 2 therebetween.

Figure 8:
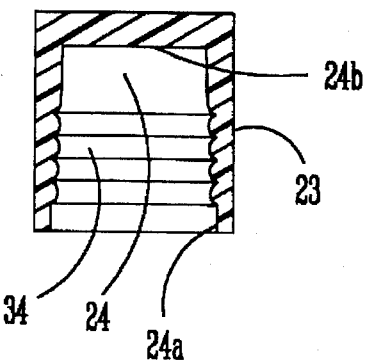
FIG. 8 is a sectional elevation of the connector member in position taken on the line 8—8 of FIG. 7.
Figure 9:
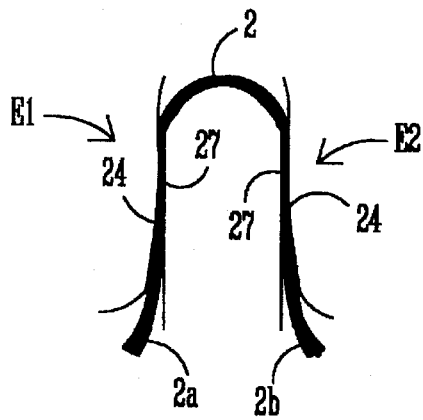
FIG. 9 is an illustration of the principal of the invention.
Figure 10:
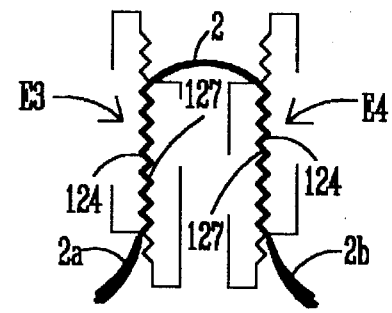
FIG. 10 is still an illustration of the principal of the invention.

Preferably, inner surface 24 further comprises a knurled surface 34, best shown in FIG. 8, defining small circumferential ridges integrally formed on inner surface 24. Similarly, outer surface 27 further comprises a knurled surface 37, best shown in FIG. 5, defining also small circumferential ridges integrally formed on outer surface 27. Both knurled surfaces 34 and 37 are to facilitate the engagement of inner surface 24 and outer surface 27 so that dental floss 2 is more securely fastened between inner surface 24 and outer surface 27. The principal of the invention of fastening one end of dental floss 2 between two mating or corresponding surfaces is best shown in FIGS. 9 and 10. In FIG. 9, dental floss 2 is securely fastened between inner surface 24 and outer surface 27 on engagement E1 and engagement E2. Although only one engagement is sufficient enough to securely fasten dental floss 2, two engagements serve reinforcement and are preferred in the present invention. The length of each engagement is preferably about one-eighth of an inch in this form of the invention. Other lengths of engagement may, of course, be used as required. FIG. 10 shows the same principal as seen in FIG. 9. In FIG. 10, an inner surface 124 and an outer surface 127 have mating surfaces defining an inner screw surface and an outer screw surface, respectively. Both inner and outer screw surfaces have screw threads formed thereon dimensioned to screw together with each other. Dental floss 2 is securely fastened between inner surface 124 and outer surface 127 on engagement E3 and engagement E4. The principal shown in FIG. 10 is identical to that of FIG. 9, except that the shapes of inner and outer surfaces 124 and 127 are inner and outer screw surfaces, respectively. Otherwise, the same principal of using mating surfaces in FIGS. 9 and 10 achieves exactly the same resultant effects and is substantially identical in operation and in structure.

Referring still to FIGS. 3, 5, 8, 9 and 10, each dental floss holder 82 also comprises connecting means for connecting the retaining means with the fastening means together to securely fasten dental floss 2 retained by the retaining means. In the preferred form of the invention the connecting means comprises inner surface 24, outer surface 27, and a connector member 23. Connector member 23 comprises preferably a generally elongated cylindrical piece of material and is also dimensioned to be easily handled by fingers. As shown best in FIGS. 5 and 8, inner surface 24 is preferably integrally formed on the internal peripheral surface of connector member 23. Also, inner surface 24 preferably comprises generally the form of a frustum having a larger diameter end 24a and a smaller diameter end 24b. Outer surface 27 is preferably integrally formed on the external peripheral surface of first member 21. Also, outer surface 27 comprises preferably a generally elongated cylindrical piece of material having a diameter substantially uniform throughout its length. The diameter of outer surface 27 is dimensioned to be slightly smaller than the diameter of end 24a and slightly larger than the diameter of end 24b. Therefore, when connector member 23 connects inner surface 24 with outer surface 27 together, end 24a will allow the insertion of outer surface 27 into inner surface 24. As outer surface 27 proceeds longitudinally a distance (preferably about one-third the longitudinal length of outer surface 27) into inner surface 24 to a position where the diameter of outer surface 27 is substantially equal to that of inner surface 24, outer surface 27 comes into contact with inner surface 24. As a result, the insertion movement of outer surface 27 is restricted by inner surface 24. Both inner surface 24 and outer surface 27 comprise any suitable materials having resilient character such as plastic and metal. Also, both first member 21 and connector member 23 comprise any rigid materials. In this form of the invention inner and outer surfaces 24 and 27 are preferably integrally formed on the internal peripheral surface of connector member 23 and external peripheral surface of first member 21, respectively. Therefore, outer surface 27 can still further proceed toward end 24b upon applying a force such as a push so that first member 21 and connector member 23 add frictional engagement between inner surface 24 and outer surface 27. The frictional engagement between inner surface 24 and outer surface 27 creates substantially no gap or space therebetween whereby dental floss 2 is effectively, securely fastened between inner surface 24 and outer surface 27.

Referring now to FIG. 5 and FIG. 6 from A to E, notch 26 is preferably formed generally on the opposite end of bottom 25 of first member 21. Slot 22 connects with notch 26 at connection line 28 remote from the opening cut of notch 26, and extends generally longitudinally from connection line 28 deeper toward bottom 25 in first member 21. In the present form of the invention outer surface 27 is preferably integrally formed on the external peripheral surface of first member 21, so slot 22 cuts through first member 21 and outer surface 27. Slot 22 is a strip of a narrow cut creating generally two parallel lines adjacent to each other closely. The perpendicular distance between the two parallel lines may be slightly smaller than, equal to, or slightly larger than the cross-sectional dimension of dental floss 2. The preferable distance between the two parallel lines of slot 22 is dimensioned to be slightly smaller than the cross-sectional dimension of dental floss 2 so that it effectively receives dental floss 2 to further facilitate the retention of dental floss 2. The main purpose of slot 22 is to prevent the lateral movement of dental floss 2 retained by first member 21. Therefore, when the distance between the two parallel lines of slot 22 is equal to or slightly larger than the cross-sectional dimension of dental floss 2, it still serves the purpose of further receiving dental floss 2. Notch 26, for facilitating the retention of dental floss 2 onto first member 21, has been defined as an annular cut through substantially the opposite end of bottom 25. Notch 26 may start from the angle of zero degree and increase to 360°, as shown in FIG. 6 from A to E. A dashed line 3 is presented to show the relative positions of connection line 28 at different degrees of the angular cut. However, the preferred angles are between 40° and 120° in the present invention. For example, when the degree is zero, as in A of FIG. 6, notch 26 functions substantially the same as slot 22 does in the slightly-smaller-than case, which will tightly receive dental floss 2 into notch 26 and slot 22. When the degree is 180°, as in C of FIG. 6, notch 26 becomes flat. When the degree is 240°, notch 26 turns downward. The longitudinal depth of notch 26 into first member 21 from the opening of notch 26 to connection line 28 is about one-sixth the longitudinal length of first member 21. The longitudinal length of slot 22 starting from connection line 28 toward bottom 25 is about one-fifth the longitudinal length of first member 21 in this form of the invention. Therefore, when the degree of notch 26 is 360°, as in E of FIG. 6, notch 26 disappears and cuts out the top portion of slot 22. The longitudinal length of slot 22 becomes one-thirtieth that of first member 21 (subtract notch 26, one-sixth the longitudinal length of first member 21, from slot 22, one-fifth the longitudinal length of first member 21). Slot 22 having one-thirtieth the longitudinal length of first member 21 can still effectively receive dental floss 2.

The method of fastening one end of dental floss 2 according to the invention may be best described with reference to FIGS. 2 through 4. The method includes first retaining one end of dental floss 2 onto first member 21 at the opposite end of bottom 25 with section 2a near bottom 25 along one side of first member 21 and section 2b along the other side of first member 21 so that dental floss 2 extends from section 2a near bottom 25, reaches generally longitudinally to the opposite end of bottom 25 along one side of first member 21, crosses generally transversely over first member 21 at the opposite end of bottom 25, and then extends generally longitudinally toward bottom 25 along the other side of first member 21 to section 2b. In the illustrated preferred form of the invention, outer surface 27 is formed on the external peripheral surface of first member 21 so that when sections 2a and 2b abut against first member 21, sections 2a and 2b must also abut against outer surface 27.

Having dental floss 2 retained on first member 21 with sections 2a and 2b against both sides of first member 21, the method continues with the step of connecting connector member 23 with first member 21 so as to connect inner surface 24 with outer surface 27 tightly together such that there is substantially no gap or space between inner surface 24 and outer surface 27 so that dental floss 2 is securely, tightly fastened between inner surface 24 and outer surface 27. In the illustrated form of the invention inner surface 24 is formed on the internal peripheral surface of connector member 23. Inner surface 24 and outer surface 27 have mating dimensions to be able to abut against each other tightly without substantially any gap or space therebetween so as to securely fasten dental floss 2.

The preferred method of fastening one end of dental floss 2 also includes the step of receiving dental floss 2 into notch 26 after retaining dental floss 2 onto first member 21 at the opposite end of bottom 25 and before connecting connector member 23 with first member 21. The method of fastening one end of dental floss 2 further includes the step of receiving dental floss 2 into slot 22 after receiving dental floss 2 into notch 26 to facilitate the retention of dental floss 2 on first member 21 and before connecting connector member 23 with first member 21. In the illustrated form of the invention notch 26 has been defined as an angular cut opening through substantially the opposite end of bottom 25 of first member 21. Slot 22 which has been defined as a strip of a narrow cut connects with notch 26 and further extends into first member 21 toward bottom 25 so that dental floss 2 is more effectively retained on first member 21. Therefore, first member 21 is ready to engage with connector member 23 to securely fasten dental floss 2 between inner surface 24 and outer surface 27.

Figure 11:
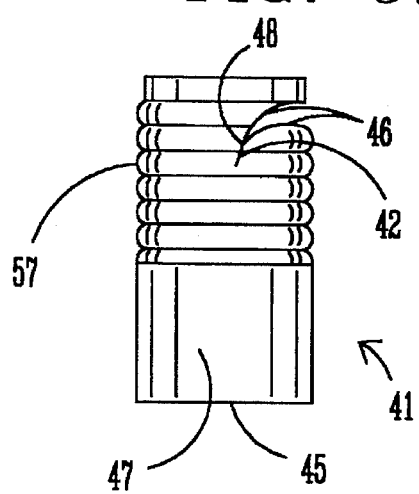
FIG. 11 is a perspective view of another embodiment of the first member.

FIG. 11 illustrates a modified embodiment of the present invention wherein an outer surface 47 having a knurled surface 57 formed thereon is preferably integrally formed on the external peripheral surface of a first member 41. First member 41 also includes a slot 42 and a notch 46. The angular cut opening of notch 46 is created on the side of first member 41. Slot 42 connects with notch 46 at a connection line 48. A bottom 45 defines the bottom of first member 41. First member 41 is substantially similar to first member 21, as seen in FIG. 4, except that the opening of notch 46 is formed on the side of first member 41 and near the opposite end of bottom 45. Otherwise, first member 41 is identical to first member 21 in operation, in resultant effects, and generally in structure. FIG. 11 shows that notch 46 may be created substantially on the side of first member 41 and near the opposite end of bottom 45.

Figure 12:
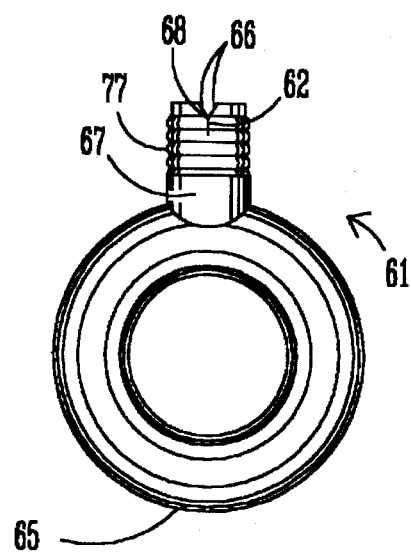
FIG. 12 is a perspective view of still another embodiment having a ring shape on the first member.

FIG. 12 illustrates a further modified embodiment of the present invention wherein a first member 61 has a notch 66 and a slot 62. First member 61 also includes an outer surface 67 and a knurled surface 77. A bottom 65 defines the bottom of first member 61. First member 61 comprises generally the form of a ring which is adapted to fit a finger so that first member 61 may be inserted into a finger when cleaning teeth. Otherwise, the embodiment of FIG. 12 is substantially identical to that of FIG. 4 in operation, in resultant effects, and generally in structure.

Based on the same principal of the present invention, FIGS. 13 through 19 illustrate embodiments having mating or corresponding surfaces defining screw surfaces, as shown in FIG. 10, to be able to screw together with each other to securely fasten one end of dental floss 2 between screw surfaces. The principal of the invention of fastening one end of dental floss 2 between mating surfaces has been shown in FIGS. 9 and 10.

Figure 13:
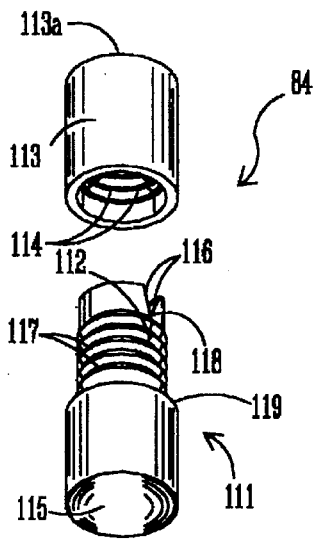
FIG. 13 is a perspective view of another embodiment based on the same principal of the invention.
Figure 14:
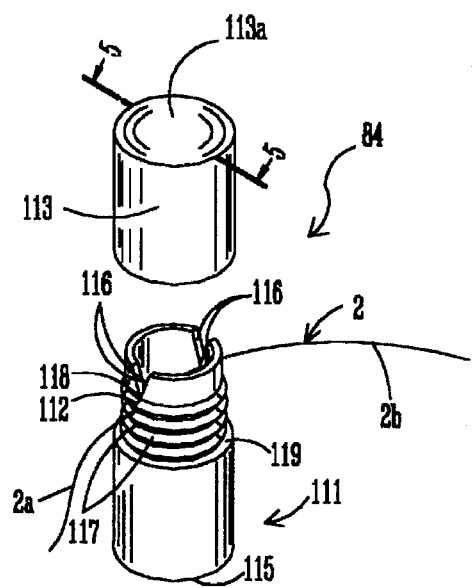
FIG. 14 is a perspective view of the embodiment in FIG. 13 with a dental floss.
Figure 15:
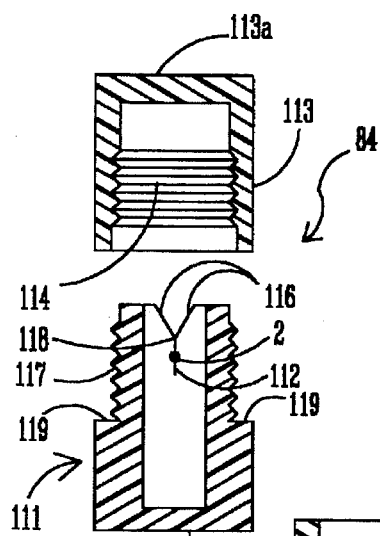
FIG. 15 is a sectional elevation of the embodiment in position taken on the line 5—5 of FIG. 14.

Referring now to FIGS. 13, 14, and 15, a dental floss holder 84 is substantially similar to dental floss holder 82, as seen in FIG. 3, generally in structure and in operation, except that the shapes of the mating surfaces in the form of screw threads. Dental floss holders 84 and 82 achieve exactly the same resultant effects. Dental floss holder 84 still comprises the retaining means, the same as dental floss holder 82 has, for retaining one end of dental floss 2. In the preferred form of the current invention the retaining means comprises a first member 111 which is preferably comprised of a generally elongated cylindrical piece of material dimensioned to be easily handled by fingers for retaining dental floss 2 onto first member 111. First member 111 has a bottom 115 defining the bottom of first member 111.

Referring again to FIGS. 13, 14, and 15, dental floss holder 84 also comprises the first receiving means, the same as dental floss holder 82 has, for receiving one end of dental floss 2 to facilitate the retention of dental floss 2. In the preferred form of the invention the first receiving means comprises a notch 116 defining an angular cut opening through substantially the opposite end of bottom 115. Dental floss holder 84 further comprises the second receiving means, the same as dental floss holder 82 has, for further receiving one end of dental floss 2 after dental floss 2 is received by the first receiving means to further facilitate the retention of dental floss 2. In the illustrated form of the invention the second receiving means comprises a slot 112 for further receiving one end of dental floss 2. Slot 112 connects with notch 116 preferably at a connection line 118 defining a line where the angular cut of notch 116 converges or meets together so that the only action required to insert dental floss 2 from notch 116 into slot 112 is a downward force to pull dental floss 2 into slot 112. Notch 116 and slot 112 are identical to notch 26 and slot 22, respectively. Notch 116 and slot 112 are still used to facilitate the retention of one end of dental floss 2.

Referring particularly to FIGS. 9, 10 and 15, dental floss holder 84 further comprises the fastening means, the same as dental floss holder 82 has, for fastening one end of dental floss 2. The fastening means includes two mating or corresponding surfaces to be able to abut against each other tightly together without substantially any gap or space therebetween to securely fasten one end of dental floss 2. In this preferred form of the invention the fastening means comprises an inner surface 114 instead of inner surface 24, as shown in FIG. 3, and a mating outer surface 117 instead of outer surface 27. Inner surface 114 and outer surface 117 have mating screw threads to be able to screw together. In this form of the invention inner surface 114 is an internal screw threads, and outer surface 117 is an external screw threads. Although inner and outer surfaces 114 and 117 are different from inner and outer surfaces 24 and 27 slightly in shapes, inner and outer surfaces 114 and 117 are still mating surfaces dimensioned to be used just like inner and outer surfaces 24 and 27. When inner and outer surfaces 114 and 117 are matingly joined, the mating screw threads screw together with each other. The mating screw threads are free to rotate relative to each other and are dimensioned to abut against each other without substantially any gap or space therebetween to securely fasten one end of dental floss 2.

Referring still to FIGS. 13, 14, and 15, dental floss holder 84 also comprises the connecting means, the same as dental floss holder 82 has, for connecting the retaining means with the fastening means together to securely fasten dental floss 2 retained by the retaining means. In the preferred form of the invention the connecting means comprises inner surface 114, outer surface 117, and a connector member 113. Connector member 113 preferably comprises a generally elongated cylindrical piece of material and is also dimensioned to be easily handled by fingers. Connector member 113 has an end 113a defining a closed end of connector member 113. Inner surface 114 is preferably integrally formed on the internal peripheral surface of connector member 113. Inner surface 114 comprises preferably a generally elongated cylindrical piece of material having a diameter substantially uniform throughout its length. Outer surface 117 is also preferably integrally formed on the external peripheral surface of first member 111. Also, outer surface 117 comprises preferably a generally elongated cylindrical piece of material having a diameter substantially uniform throughout its length. The diameters of inner surface 114 and outer surface 117 are dimensioned to be able to screw together with each other so as to create substantially no gap or space therebetween. Therefore, when connector member 113 connects inner and outer surfaces 114 and 117 together, outer surface 117 will be able to insert into inner surface 114. As outer surface 117 proceeds longitudinally toward end 113a, outer surface 117 comes into contact with end 113a to stop forward rotating movement. There is also an alternate way to restrict the forward rotating movement of outer surface 117. A stop 119 defining a circumferential projection formed on first member 111 may be used to stop the forward rotating movement of outer surface 117 in the case where connector member 113 comes into contact with stop 119 before outer surface 117 reaches end 113a. However, stop 119 is preferred in this form of the invention because the contact engagement between connector member 113 and stop 119 may be used to add an extra engagement length to enhance the fastening of dental floss 2. The abutment between inner surface 114 and outer surface 117 creates substantially no gap or space therebetween whereby one end of dental floss 2 is effectively, securely fastened between inner surface 114 and outer surface 117. The method of using dental floss holder 84 to fasten one end of dental floss 2 is identical to the method described above for using dental floss holder 82.

Figure 16:
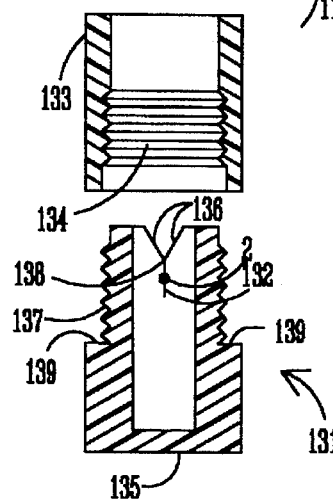
FIG. 16 is a sectional elevation of an embodiment similar to that of FIG. 15 but without a closed end on the connector member.

FIG. 16 illustrates an embodiment similar to that of FIG. 15, except that a connector member 133 does not have end 113a as connector member 113 does; that is, connector member 133 is a through passage tubular configuration. Connector member 133 is for connecting an inner surface 134 with an outer surface 137. Connector member 133 will stop at a stop 139 to securely fasten one end of dental floss 2 between inner and outer surfaces 134 and 137. The embodiment of FIG. 16 is substantially identical to that of FIG. 15 in structure, in operation and in resultant effects.

Figure 17:
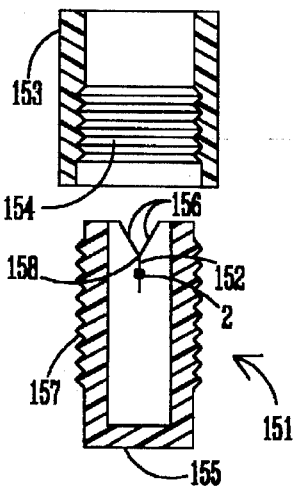
FIG. 17 is a sectional elevation of an embodiment similar to that of FIG. 16 but without a stop on the first member.

FIG. 17 illustrates a further embodiment similar to that of FIG. 16, except that a first member 151 does not have stop 139 as first member 131 does. When a connector member 153 connects an inner surface 154 with an outer surface 157, they may stop at any point where one end of dental floss 2 is substantially fastened between inner and outer surfaces 154 and 157. The dimensions of inner and outer surfaces 154 and 157 are configured to abut against each other tightly without substantially any gap or space therebetween. Therefore, when dental floss 2 is fastened between inner and outer surfaces 154 and 157, the engagement between dental floss 2 and inner and outer surfaces 154 and 157 will then generally restrict the longitudinally free rotating movement. Preferably, the full longitudinal length of first member 151 is longer than that of connector member 153 to facilitate the rotating movement. The embodiment of FIG. 17 is substantially identical to that of FIG. 16 in operation, in resultant effects and generally in structure.

Figure 18:
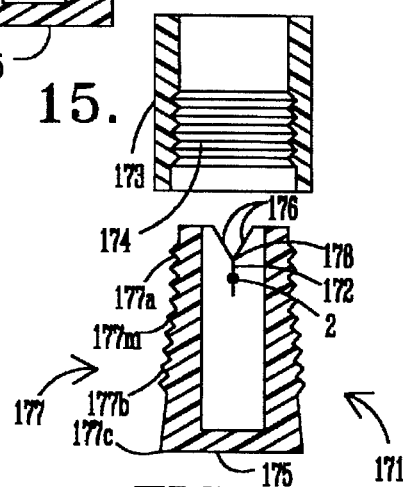
FIG. 18 is a sectional elevation of an embodiment similar to that of FIG. 17 but with the form of a truncated conical configuration in the first member.

FIG. 18 illustrates a further embodiment similar to that of FIG. 17, except that an outer surface 177 is a generally truncated conical configuration preferably formed on the external peripheral surface of a first member 171; that is, a first section 177a of outer surface 177 has a generally uniform diameter and a second section 177b has the form of a frustum having a larger diameter end 177c and a smaller diameter end 177m. First section 177a and second section 177b connect at end 177m. Therefore, the diameter of end 177m is also the diameter of first section 177a. End 177m is about at the middle of outer surface 177. An inner surface 174 which has a generally uniform diameter is dimensioned to mate with first section 177a like the mating dimensions in FIG. 17. Inner surface 174 is preferably formed on the internal peripheral surface of a connector member 173. Therefore, when outer surface 177 enters into inner surface 174, first section 177a proceeds without much restriction until inner surface 174 comes into contact with second section 177b. Both inner surface 174 and outer surface 177 comprise any suitable materials having resilient character such as plastic and metal. Also, both first member 171 and connector member 173 comprise any rigid materials. In this form of the invention inner and outer surfaces 174 and 177 are preferably integrally formed on the internal peripheral surface of connector member 173 and external peripheral surface of first member 171, respectively. Therefore, outer surface 177 can still further proceed forward, but first member 171 and connector member 173 add frictional engagement between inner surface 174 and second section 177b of outer surface 177. The frictional engagement between inner surface 174 and second section 177b causes dental floss 2 to be extremely tightly fastened between inner surface 174 and outer surface 177. The embodiment of FIG. 18 is substantially identical to that of FIG. 17 in operation, in resultant effects and generally in structure.

Figure 19:
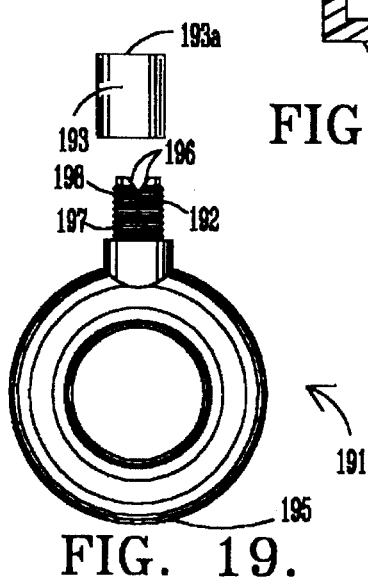
FIG. 19 is a perspective view of an embodiment similar to that of FIG. 13 but with a ring shape on the first member.

FIG. 19 illustrates a further embodiment similar to that of FIG. 13, except that a first member 191 preferably comprises generally the form of a ring which is adapted to fit a finger so that first member 191 may be inserted into a finger when cleaning teeth. The embodiment of FIG. 19 also includes a connector member 193 comprising preferably a generally cylindrical piece of material. FIG. 19 shows that first member 191 may comprise the form of a ring. Similarly, connector member 193 may also comprise the form of a ring as required. It is understood that any general, suitable piece of materials having any suitable shapes such as a cylinder and a ring dimensioned to be handled by fingers may be used. It is also understood that the form of a ring or any suitable configurations may be formed on either first member 191 or connector member 193. Otherwise, the embodiment of FIG. 19 is substantially identical to that of FIG. 13 in operation, in resultant effects and generally in structure.

Although the description above contains many specifications, these should not be construed as limiting the scope of the invention but as merely providing illustrations of some of the presently preferred embodiments of this invention. Thus the scope of the invention should be determined by the appended claims and their legal equivalents, rather than by the examples given.

We claim:

1. A dental floss holder for fastening one end of a dental floss, said holder comprising:

a connector member having a generally frustum surface thereon; and a first member adapted to be handled by fingers, said first member having a generally uniform surface for said frustum surface of said connector member so that when said frustum surface of said connector member engagingly connects with said uniform surface of said first member, the floss is fastened between said frustum surface and said uniform surface, whereby when the floss is fastened between said surfaces, said holder having the floss fastened therein is manipulated by a hand in lieu of winding the floss around a finger for teeth cleaning.

2. The holder of claim 1, wherein said first member further comprises a notch defining a substantially angular cut formed substantially on one end of said first member, whereby the floss may be inserted into said notch to facilitate the retention of the floss.

3. The holder of claim 2, wherein said first member further comprises a slot connecting to said notch, said slot deepening into said first member, whereby the floss may be inserted into said slot for facilitating the retention of the floss.

4. The holder of claim 1, wherein said uniform surface has generally a uniform diameter throughout its length.

5. The holder of claim 1, wherein at least one of said first member and said connector member is of a generally elongated configuration, such as a cylindrical configuration.

6. The holder of claim 1, wherein at least one of said first member and said connector member is of a substantial ring configuration adapted to be fitted into a finger.

7. The holder of claim 1, wherein at least one of said uniform and frustum surfaces further comprises a generally knurled surface.

8. A dental floss holder for fastening one end of a length of dental floss, said holder comprising:

a connector member having an inner surface thereon; and a first member adapted to be handled by fingers, said first member having a mating outer surface so that when said inner surface of said connector member and said outer surface of said first member engagingly connect with each other, the floss is fastened between said surfaces, whereby when the floss is fastened between said surfaces, said holder having the floss fastened therein is manipulated by a hand for teeth cleaning.

9. The holder of claim 8, wherein said inner and outer surfaces are threaded surfaces and said first member further comprises a substantially V-shaped notch formed substantially on one end of said first member and a slot connecting to said notch, said slot deepening into said first member.

10. The holder of claim 8, wherein said first member further comprises a notch defining a substantially angular cut formed substantially on one end of said first member, whereby the floss may be inserted into said notch to facilitate the retention of the floss.

11. The holder of claim 10, wherein said first member further comprises a slot connecting to said notch, said slot deepening into said first member, whereby the floss may be inserted into said slot for facilitating the retention of the floss.

12. The holder of claim 8, wherein said surfaces are a generally frustum surface and a generally uniform surface.

13. The holder of claim 8, wherein at least one of said first member and said connector member is of a generally elongated configuration, such as a cylindrical configuration.

14. The holder of claim 8, wherein at least one of said first member and said connector member is of a substantial ring configuration adapted to be fitted into a finger.

15. A dental floss device for fastening a length of dental floss, said device comprising:

two separate dental floss holders, each of said holders for fastening each end of the floss, at least one of said holders comprising:

a connector member having an inner surface thereon; and a first member having an outer surface for said inner surface of said connector member so that when said inner surface of said connector member and said outer surface of said first member engagingly connect with each other, the floss is fastened between said inner and outer surfaces of said connector and first members, whereby when each end of the floss is fastened in each of said holders, each of said holders is manipulated by a hand in a spaced apart relationship for teeth cleaning.

16. The device of claim 15, wherein said surfaces of said at least one of said holders are threaded surfaces.

17. The device of claim 15, wherein said first member of said at least one of said holders further comprises a notch, said notch defining a substantially angular cut formed substantially on one end of said first member, whereby the floss may be inserted into said notch for facilitating the retention of the floss.

18. The device of claim 17, wherein said first member further comprises a slot connecting to said notch, said slot deepening into said first member, whereby the floss may be inserted into said slot for facilitating the retention of the floss.

19. The device of claim 15, wherein the surfaces of said at least one of said holders are a generally frustum surface and a generally uniform surface.

20. The device of claim 15, wherein at least one of said first member and said connector member of said at least one of said holders is of a generally elongated configuration, such as a cylindrical configuration, adapted to be handled by fingers.

21. The device of claim 15, wherein at least one of said first member and said connector member of said at least one of said holders is of a substantial ring configuration adapted to be fitted into a finger.

22. A dental floss holder for fastening one end of a length of dental floss, said holder comprising:

a connector member;

a first member adapted to be handled by fingers, whereby the floss may be held by fingers against both sides of said first member to facilitate the retention of the floss;

an inner surface; and an outer surface which is matingly engageable with said inner surface, one of said surfaces formed on said connector member and the other said surface formed on said first member so that when said surfaces of said connector and first members engagingly connect with each other, the floss is fastened between said surfaces, whereby when the floss is fastened between said surfaces, said holder having the floss fastened therein is manipulated by a hand in lieu of winding the floss around a finger for teeth cleaning.

23. The holder of claim 22, wherein said first member further comprises a notch defining a substantially angular cut formed substantially on one end of said first member, whereby the floss may be inserted into said notch to facilitate the retention of the floss.

24. A method of fastening one end of a length of dental floss, which comprises:

retaining the floss on a first member having an outer surface thereon; and connecting a connector member having a mating inner surface with said outer surface to fasten the floss between said outer and inner surfaces, whereby said first member and said connector member having the floss fastened therein are held by a hand in lieu of winding the floss around a finger for teeth cleaning.

25. The method of claim 24, wherein the retaining step is performed by placing the floss into a notch of said first member.

26. The method of claim 24, wherein the connecting step is performed by connecting a generally uniform surface with a generally frustum surface.

\* \* \* \* \*